United States Patent [19]

Greenbaum

[11] 4,442,211

[45] Apr. 10, 1984

[54] METHOD FOR PRODUCING HYDROGEN AND OXYGEN BY USE OF ALGAE

[75] Inventor: Elias Greenbaum, Oak Ridge, Tenn.

[73] Assignee: The United States of America as represented by the United States Department of Energy, Washington, D.C.

[21] Appl. No.: 388,872

[22] Filed: Jun. 16, 1982

[51] Int. Cl.³ .................... C12P 3/00; C12N 13/00; C12N 1/12; A01H 13/00
[52] U.S. Cl. ................................. 435/168; 435/173; 435/257; 435/946; 47/1.4
[58] Field of Search ............. 435/168, 173, 257, 946; 47/1.4

[56] References Cited

U.S. PATENT DOCUMENTS 4,010,076  3/1977  Weetall ........................... 435/173
4,148,690  4/1979  Weetall ........................... 435/168

OTHER PUBLICATIONS

Weissman et al., "Hydrogen Production by Nitrogen-Starved Cultures of Anabaena Cylindrica", Applied and Environmental Microbiology 33(1) (1977) pp. 123-131.

Bothe, "Hydrogen Production by Algae", Experientia 38 (1/82) pp. 59-66.

Greenbaum, "Simultaneous Photoproduction of Hydrogen and Oxygen by Photosynthesis", Biotechnology and Bioengineering Symposium 10 (1980) pp. 1-13.

Zajic et al., "Microbial Hydrogen Production from Replenishable Resources", International Journal of Hydrogen Energy 4 (1979) pp. 385-402.

Primary Examiner—Thomas G. Wiseman
Assistant Examiner—John Edward Tarcza
Attorney, Agent, or Firm—Edwin D. Grant; Stephen D. Hamel; Michael F. Esposito

[57] ABSTRACT

Efficiency of process for producing $H_2$ by subjecting algae in an aqueous phase to light irradiation is increased by culturing algae which has been bleached during a first period of irradiation in a culture medium in an aerobic atmosphere until it has regained color and then subjecting this algae to a second period of irradiation wherein hydrogen is produced at an enhanced rate.

8 Claims, 3 Drawing Figures

METHOD FOR PRODUCING HYDROGEN AND OXYGEN BY USE OF ALGAE

BACKGROUND OF THE INVENTION

This invention, which resulted from a contract with the United State Department of Energy, relates to a process for producing hydrogen and oxygen by exposing algae in an aqueous phase to light under anaerobic conditions.

It has been demonstrated that certain algae, when placed in an aqueous phase and exposed to light in the absence of carbon dioxide and oxygen, split water into molecular hydrogen and oxygen. However, the proposed use of algae and solar energy to produce hydrogen for fuel has not yet become economically feasible because the algae used heretofore provide low hydrogen yields and also lose their color (or chlorophyll) after a relatively short exposure to light and thus become ineffective.

SUMMARY OF THE INVENTION

It is therefore an object of this invention to increase the efficiency of the process of producing hydrogen by irradiating algae with light.

Another object of the invention is to provide a process which extends the time during which algae can effectively produce hydrogen under light stimulation.

In accordance with the invention, these objects are achieved by (1) subjecting algae in an aqueous phase to light in an environment substantially free of $CO_2$ and atmospheric $O_2$ to produce $H_2$ and $O_2$ by splitting water molecules during a first period of time of sufficient duration to produce a physiological stress on said algae, (2) culturing said algae in culture medium in an aerobic atmosphere during a second period of time, and (3) subjecting said algae in an aqueous phase to light in an environment substantially free of $CO_2$ and atmospheric $O_2$ to produce $H_2$ and $O_2$ during a third period of time at an enhanced rate of production.

DETAILED DESCRIPTION OF THE INVENTION

Figure 1:
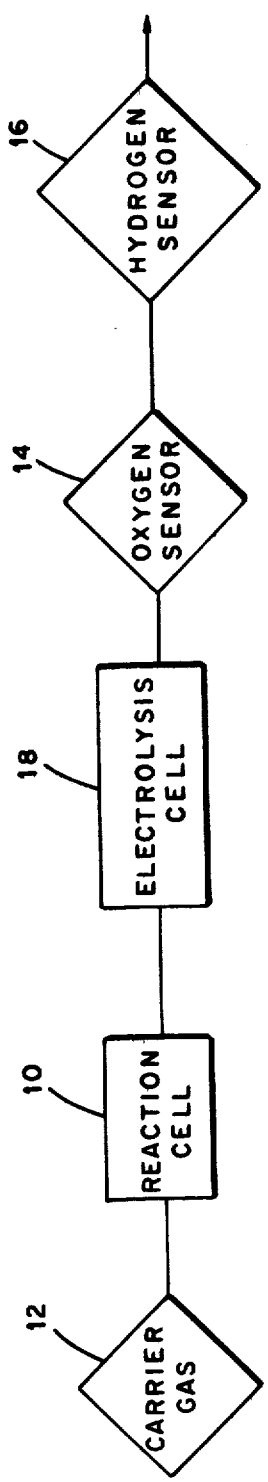
FIG. 1 is a schematic representation of an apparatus used to measure the amounts of hydrogen and oxygen produced by algae during experimental tests of the process of this invention.

FIG. 1 illustrates an apparatus that was used in testing the amounts of $H_2$ and $O_2$ produced by algae when irradiated with light in both a conventional process and the improved process of the invention. Reference number 10 designates a reaction cell in which a selected algae sample was irradiated with light in an environment substantially free of $CO_2$ and atmospheric $O_2$, this environment being maintained by passing an inert gas (e.g., helium) through the cell from a pressurized source 12. The inert gas also served as a carrier for removing from cell 10 all $H_2$ and $O_2$ generated by the splitting of $H_2O$ molecules in the aqueous medium (or phase) in which the algae sample was held along with a growth medium. The amounts of $H_2$ and $O_2$ produced under different process conditions which will be described hereinafter were respectively measured by means of an oxygen sensor 14 and a hydrogen sensor 16, the former being a Hersch electrogalvanic cell and the latter being a tin oxide gas-sensitive semiconductor. Calibration of the $H_2$ and $O_2$ sensors was achieved with an electrolysis cell 18 placed in tandem with reaction cell 10 as illustrated in the drawing. By electrolyzing water in cell 18 with a measured current, a known amount of hydrogen and oxygen was introduced in the stream of carrier gas in accordance with Faraday's law of electrochemical equivalance.

Illumination of algae samples was achieved with a lamp which was equipped with a tungsten filament and a conical reflector and which produced an irradiance of 125 $W/m^2$ at the surface of the reactance cell. The tungsten lamp was turned on and off at periodic intervals by means of a programmable circuit controller. Rates of gas production were measured by sensors 14,16 during the "on" portion of the cycle, and during the "off" portion of the cycle the baselines for the oxygen and hydrogen detector outputs were re-established, thereby correcting for any long term drift in the measuring system.

The data graphically illustrated in FIGS. 1 and 2 and the data shown in a table presented hereinafter were obtained in experimental tests which used samples containing *Chlamydomonas reinhardtii* (wild type+obtained from Carolina Biological Supply Co., their catalogue number 15-2040) in an aqueous growth medium. More specifically, each of the test samples contained 7.9 mg of the aforesaid algae per 5 ml of a culture medium having the composition shown in the following tables:

| Culture Medium | |
|---|---|
| Per liter: | |
| Beijerinck's solution | 30 ml |
| Phosphate solution | 50 ml |
| Trace elements solution | 1 ml |
| $H_2O$ | 899 ml |
| Beijerinck's Solution | |
| $NH_4Cl$ | 8.0 g |
| $CaCl_2.2H_2O$ | 1.0 g |
| $MgSO_4.7H_2O$ | 2.0 g |
| $H_2O$ | to 1 liter |
| Phosphate Solution | |
| $K_2HPO_4$ | 14.34 g |
| $KH_2PO_4$ | 7.26 g |
| $H_2O$ | to 1 liter |
| Trace Elements Solutions | |
| EDTA, diosodium salt | 50.0 g |
| $ZnSO_4.7H_2O$ | 22.0 g |
| $H_3BO_4$ | 11.4 g |
| $MnCl_2.4H_2O$ | 5.06 g |
| $FeSO_4.7H_2O$ | 4.99 g |
| $CoCl_2.6H_2O$ | 1.61 g |
| $CuSO_4.5H_2O$ | 1.57 g |
| $(NH_4)_6Mo_7O_{24}.4H_2O$ | 1.10 g |
| $H_2O$ | to 1 liter |

Figure 2:
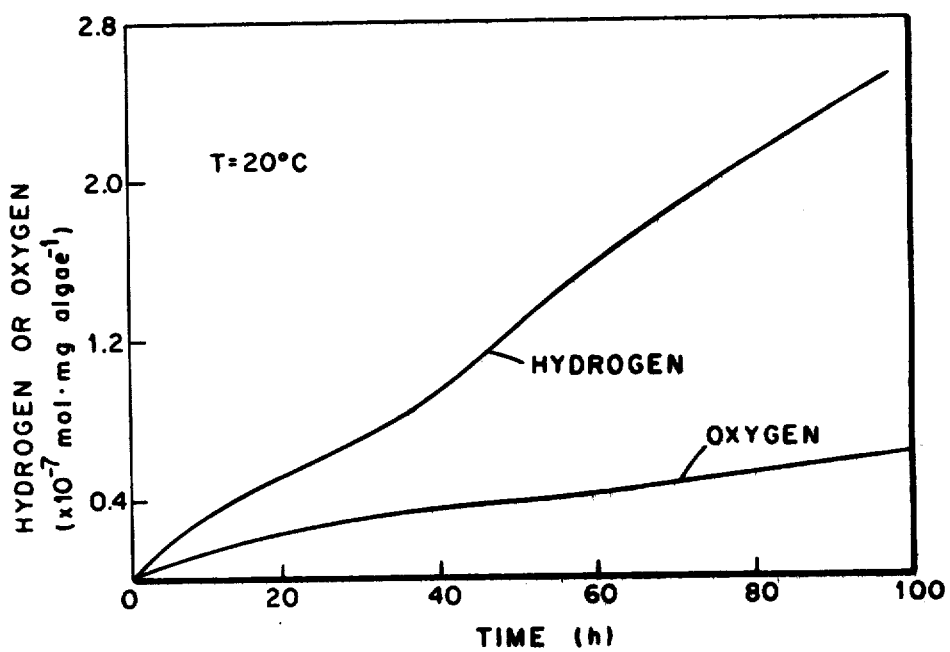
FIG. 2 is a graphical plot of hydrogen and oxygen production versus time in a conventional process which utilizes *Chlamydomonas reinhardtii* algae.

FIG. 2 shows the production of $H_2$ and $O_2$ achieved by irradiating a 5 ml sample of the above-described culture medium which was inoculated with 7.9 mg of *Chlamydomonas reinhardtii* for a period of 100 hours, the tungsten used for irradiating the sample being alternatley turned on for 3 hours and off for 1 hour during this period. Each data point shown in FIG. 2 was obtained by subjecting the algae to a 3-hour period of irradiation and adding the yield to the previous cumulative yield. The data points of FIG. 2 are presented in tabular form in the following table wherein hydrogen production during the first 100-hour period is given in the column with the heading $F(H_2)$ and oxygen production during the same period is given in the column with the heading $F(O_2)$. Units for the numerical values in the columns of the table are $10^{-7}$ mole of gas·mg algae$^{-1}$ on a dry weight basis.

Comparison of Hydrogen and Oxygen Photoproduction Yields in First and Second Generation Cells of *Chlamydomonas reinhardtii*

| Irradiation No. | $F(H_2)$ | $F(O_2)$ | $S(H_2)$ | $S(O_2)$ | $\dfrac{S(H_2)}{F(H_2)}$ | $\dfrac{S(O_2)}{F(O_2)}$ |
|---|---|---|---|---|---|---|
| 1 | 0.22 | 0.10 | 3.30 | 1.50 | 15.0 | 15.0 |
| 2 | 0.40 | 0.18 | 4.62 | 2.80 | 11.6 | 15.6 |
| 3 | 0.56 | 0.24 | 5.90 | 3.90 | 10.5 | 16.3 |
| 4 | 0.69 | 0.29 | 7.52 | 4.71 | 10.9 | 16.2 |
| 5 | 0.88 | 0.32 | 8.09 | 5.50 | 9.2 | 17.2 |
| 6 | 1.09 | 0.36 | 8.51 | 6.19 | 7.8 | 17.2 |
| 7 | 1.37 | 0.39 | 8.90 | 6.88 | 6.5 | 17.6 |
| 8 | 1.62 | 0.43 | 9.68 | 7.11 | 6.0 | 16.5 |
| 9 | 1.84 | 0.47 | 9.88 | 7.41 | 5.4 | 15.8 |
| 10 | 2.02 | 0.50 | 10.05 | 7.60 | 5.0 | 15.2 |
| 11 | 2.22 | 0.54 | 10.15 | 7.81 | 4.6 | 14.5 |
| 12 | 2.40 | 0.58 | 10.69 | 7.99 | 4.5 | 13.8 |

Figure 3:
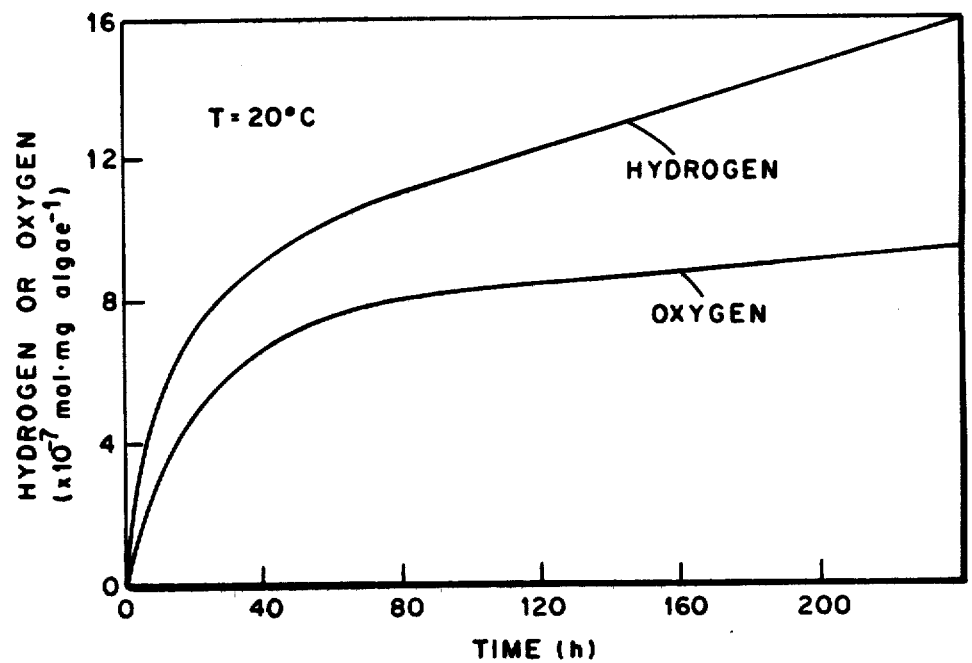
FIG. 3 is a graphical representation of hydrogen and oxygen production versus time in a process which utilizes the same *Chlamydomonas reinhardtii* algae in accordance with the principles of the invention.

At the end of a 100-hour period of irradiation of the *Chlamydomonas reinhardtii* culture in the cell 10 maintained free of atmospheric oxygen by means of the helium sweep gas passed therethrough, the algae had acquired a bleached appearance which indicated the loss of chlorophyll. The bleached algae were then removed from cell 10 and used as inoculum in fresh growth medium having the composition which has been described, the inoculated medium being exposed to atmospheric oxygen after the algae were added thereto. After a period of about 24 hours, this culture had regained its original green color, indicating that the algae sample remaining after the first 100-hour period of irradiation still contained viable, surviving cells. The new strain of re-greened second generation *Chlamydomonas reinhardtii* cells was then tested for hydrogen and oxygen producing capabilities for a second period of 240 hours in the test apparatus illustrated in FIG. 1, under the same conditions described in connection with the first 100-hour period of irradiation. The results of this second period of irradiation are shown in FIG. 3 for a culture containing the same weight ratio of algae per ml of culture medium that was used in the first irradiation period, and the data points indicated in the graph of FIG. 3 are recorded in the table presented hereinabove under the columns respectively designated $S(H_2)$ for hydrogen production and $S(O_2)$ for oxygen production. The columns on the right in the aforesaid table which have the heads $S(H_2)/F(H_2)$ and $S(O_2)/F(O_2)$, respectively, show the ratios of hydrogen and oxygen productions generated by the second generation *Chlamydomonas reinhardtii* cells to those of the algae cells employed in the first 100-hour period of irradiation. It can be seen that in all cases these ratios are greater than unity, indicating that an improvement in the production of hydrogen and oxygen is obtained by use of regenerated algae. In addition to the improved yields, the second generation cells maintained their green color at the end of the 240-hour irradiation period, which indicated better survivability of these cells under prolonged anaerobiosis. It can be anticipated that *Chlamydomonas reinhardtii* repeatedly subjected to physiological stress by light irradiation and regenerated in fresh culture medium will produce even greater hydrogen and oxygen yields.

Various eukaryotic and prokaryotic algae can be used to produce hydrogen and oxygen in accordance with the method of this invention, such as, for example, Scenedesmus, Kirchneriella, Collastrum, and Chorella. As will be understood by persons skilled in the art to which the invention pertains, different culture media will be used with the different algae. For example, if Scenedesmus is used in the process of the invention, the culture medium which has been described will be modified as follows:

$KNO_3$: 0.809 gms
NaCl: 0.468 gms
$Na_2HPO_4 \cdot 2H_2O$: 0.178 gms
$NaH_2PO_4 \cdot 2H_2O$: 0.468 gms
$CaCl_2 \cdot 6H_2O$: 0.022 gms
$MgSO_4 \cdot 7H_2O$: 0.247 gms
Versene: 0.020 gms
$FeSO_4 \cdot 7H_2O$: 0.01 gms
$MnCl_2 \cdot 4H_2O$: 0.2 ml of a 0.1% stock
$ZnSO_4 \cdot 7H_2O$: 0.1 ml of a 0.1% stock
$H_2O$: to 1 liter In all instances, the algae used will be regenerated after a first irradiation period in which of irradiation when it has been subjected to physiological stress, and the algae will then be used again to produce hydrogen and oxygen at an enhanced rate of production.

Although the invention is not to be construed as being limited to a particular theory with respect to the reason for its utility, a simple explanation is suggested for the increased hydrogen and oxygen production obtained by repeated irradiation of a selected alga and regeneration of the alga after it has lost its color. It may be that among wild-type algae cultures of a given species, there is a heterogeneity of algae with respect to hydrogen and oxygen photo-generation capabilities, and prolonged periods of irradiation by light energy (which may be of different wavelengths) can be used to select the organisms that survive best under the conditions of physiological stress.

What is claimed is:

1. A method of producing $H_2$ and $O_2$ by use of algae and light comprising the following steps in the sequence set forth:
   (1) subjecting algae in an aqueous phase to light in an environment substantially free of $CO_2$ and atmospheric $O_2$ to produce $H_2$ and $O_2$ by the action of the light-stimulated algae in splitting water molecules during a first period of time of sufficient duration to produce a physiological stress on said algae;
   (2) culturing said algae in culture medium in an aerobic atmosphere during a second period of time sufficient to remove said physiological stress; and
   (3) subjecting said algae in an aqueous phase to light in an environment substantially free of $CO_2$ and atmospheric $O_2$ during a third period of time at an enhanced rate of production of $H_2$ and $O_2$ compared to that occurring during said first time period of step (1).

2. The method of claim 1 wherein steps (2) and (3) thereof are repeated.

3. The method of claim 1 wherein irradiation of said algae in step (1) thereof is terminated when a predetermined loss of chlorophyll occurs in said algae.

4. The method of claim 1 wherein irradiation of said algae in step (1) thereof is terminated when a predetermined diminution in the production of $H_2$ and $O_2$ occurs.

5. The method of claim 1 wherein said algae are eukaryotic algae.

6. The method of claim 1 wherein said algae are prokaryotic algae.

7. The method of claim 1 wherein said algae are selected from the group consisting of Chlamydomonas, Scenedesmus, Kirchneriella, Collastrum, and Chorella algae.

8. The method of claim 7 wherein said algae are Chlamydomonas algae.

* * * * *